United States Patent
Hefetz et al.

(10) Patent No.: US 7,332,724 B2
(45) Date of Patent: Feb. 19, 2008

(54) METHOD AND APPARATUS FOR ACQUIRING RADIATION DATA

(75) Inventors: Yaron Hefetz, Herzeliya (IL); Hernan Altman, Haifa (IL)

(73) Assignee: General Electric Company, Schenectady, NY (US)

(*) Notice: Subject to any disclaimer, the term of this patent is extended or adjusted under 35 U.S.C. 154(b) by 190 days.

(21) Appl. No.: 11/189,451

(22) Filed: Jul. 26, 2005

(65) Prior Publication Data

US 2007/0023669 A1 Feb. 1, 2007

(51) Int. Cl.
*G01J 1/24* (2006.01)

(52) U.S. Cl. .................. 250/370.06; 250/370.09; 250/370.13; 250/371; 378/5; 378/63; 378/98.6

(58) Field of Classification Search .............. None
See application file for complete search history.

(56) References Cited

U.S. PATENT DOCUMENTS

| | | | |
|---|---|---|---|
| 4,527,063 A * | 7/1985 | Kronenberg et al. ... | 250/370.06 |
| 5,304,808 A | 4/1994 | Odell | |
| 5,365,069 A | 11/1994 | Eisen et al. | |
| 5,376,795 A | 12/1994 | Hasegawa | |
| 5,587,585 A | 12/1996 | Eisen et al. | |
| 5,939,724 A | 8/1999 | Eisen et al. | |
| 5,943,388 A | 8/1999 | Tuemer | |
| 6,246,747 B1 | 6/2001 | Wear et al. | |
| 6,248,990 B1 | 6/2001 | Pyyhtia et al. | |
| 6,310,349 B1 * | 10/2001 | Wong et al. ............ | 250/363.09 |
| 6,388,258 B1 | 5/2002 | Berlad et al. | |
| 6,399,951 B1 * | 6/2002 | Paulus et al. .......... | 250/370.13 |
| 6,449,331 B1 * | 9/2002 | Nutt et al. .............. | 378/19 |
| 6,678,039 B2 * | 1/2004 | Charbon .................. | 356/5.01 |
| 6,759,658 B2 * | 7/2004 | Overdick et al. ........ | 250/336.1 |
| 6,847,040 B2 * | 1/2005 | Strommer .............. | 250/370.09 |
| 7,138,635 B2 * | 11/2006 | Heismann .............. | 250/370.09 |
| 7,170,972 B2 * | 1/2007 | Altman .................. | 378/62 |
| 2003/0179853 A1 * | 9/2003 | Amemiya et al. ....... | 378/63 |
| 2004/0262525 A1 * | 12/2004 | Yunker et al. .......... | 250/363.08 |
| 2005/0105687 A1 | 5/2005 | Heismann | |
| 2005/0157839 A1 * | 7/2005 | Altman .................. | 378/4 |
| 2006/0113482 A1 * | 6/2006 | Pelizzari et al. ........ | 250/370.09 |

* cited by examiner

*Primary Examiner*—David Porta
*Assistant Examiner*—Casey Bryant
(74) *Attorney, Agent, or Firm*—The Small Patent Law Group LLP; Dean D. Small

(57) ABSTRACT

Method and apparatus for sensing and acquiring radiation data comprises sensing radiation events with a multi-modality detector. The detector comprises solid state crystals forming a matrix of pixels which may be arranged in rows and columns, and has a radiation detection field for sensing radiation events. The radiation events for each pixel are counted by an electronic module attached to each pixel. The electronic module comprises a threshold analyzer for analyzing the radiation events. The threshold analyzer identifies valid events by comparing an energy level associated with the radiation event to a predetermined threshold. The electronic module further comprises at least a first counter for counting the valid events.

20 Claims, 10 Drawing Sheets

METHOD AND APPARATUS FOR ACQUIRING RADIATION DATA

BACKGROUND OF THE INVENTION

This invention relates generally to detectors used in imaging systems, and more particularly, to solid state detectors configured to acquire multi-modality image data.

The cost of imaging systems is often prohibitive. Therefore, multi-modality imaging systems which are capable of scanning using different modalities, such as Positron Emission Tomography (PET), Single Positron emission tomography (SPECT), Nuclear Medicine (NM), Computed Tomography (CT), static X-ray imaging, and dynamic (Fluoroscopy) X-ray imaging are desirable. Also, a patient may be better diagnosed by comparing images acquired using different modalities. Unfortunately, it is often difficult to achieve the same view of a patient's anatomy using two different acquisition systems. Also, currently available multi-modality imaging systems often use multiple detectors with each detector being dedicated to a specific modality, limiting the flexibility of the system.

With current systems, when acquiring CT scans, the flux, or count rate, of X-ray photons often exceeds the system's capacity for counting the photons. For example, the photon flux for diagnostic CT may reach 100 MHz. Therefore, currently available solid state detectors which acquire CT data are used in current mode. Each pixel has a corresponding data channel. The signal is input to a current integrator, and then converted with an analog to digital converter (ADC). An average number of photons for a period of time are provided rather than a precise count. Current mode detection also adds noise to the signal and may require a high X-ray dose which both adversely effects living tissue and necessitates a large, expensive X-ray tube that consumes a large amount of energy and produces a large amount of heat requiring additional cooling systems. In addition, the ADC needed to provide a high level of accuracy is expensive.

When acquiring SPECT or NM data, each pixel has a corresponding data channel. The input signal is analyzed and compared to an energy range. If the input signal is less than a minimum energy value or greater than a maximum value, the signal may be rejected. Valid signals are digitized, using ADC for several or all of the pixels.

Therefore, a need exists for a system capable of acquiring patient data representative of more than one type of radiation data, which increases the flexibility and accuracy with which patient data is acquired and to address the problems noted above. Certain embodiments of the present invention are intended to meet these needs and other objectives that will become apparent from the description and drawings set forth below.

BRIEF DESCRIPTION OF THE INVENTION

A detector for sensing and acquiring radiation data comprises solid state crystals forming a matrix of pixels. The detector has a radiation sensing face for sensing radiation events. An electronic module is attached to each pixel for counting the radiation events for each pixel. The electronic module comprises a threshold analyzer for analyzing the radiation events. The threshold analyzer identifies valid events by comparing an energy level associated with the radiation event to a predetermined threshold. The electronic module further comprises at least a first counter for counting the valid events.

A system for sensing and acquiring radiation data comprises a detector comprising solid state crystals which form a matrix of pixels in rows and columns. The detector has a radiation sensing face for sensing radiation events, and further comprises electronic modules interconnected with the solid state crystals. The electronic modules comprise components for counting different types of radiation events. A gantry holds the detector in a position with respect to an object, and a work station receives signal data representative of the radiation events.

A method for acquiring radiation events comprises detecting radiation events with a solid state detector comprising a matrix of pixels. The method counts the radiation events at each of the pixels with a dedicated counter. Each of the pixels are interconnected with the dedicated counter.

The foregoing summary, as well as the following detailed description of certain embodiments of the present invention, will be better understood when read in conjunction with the appended drawings. It should be understood that the present invention is not limited to the arrangements and instrumentality shown in the attached drawings.

DETAILED DESCRIPTION OF THE INVENTION

Although the present invention is described in the context of an exemplary C-arm gantry, it should be understood that any configuration of gantry capable of performing the functions described herein is contemplated as being used.

Figure 1:
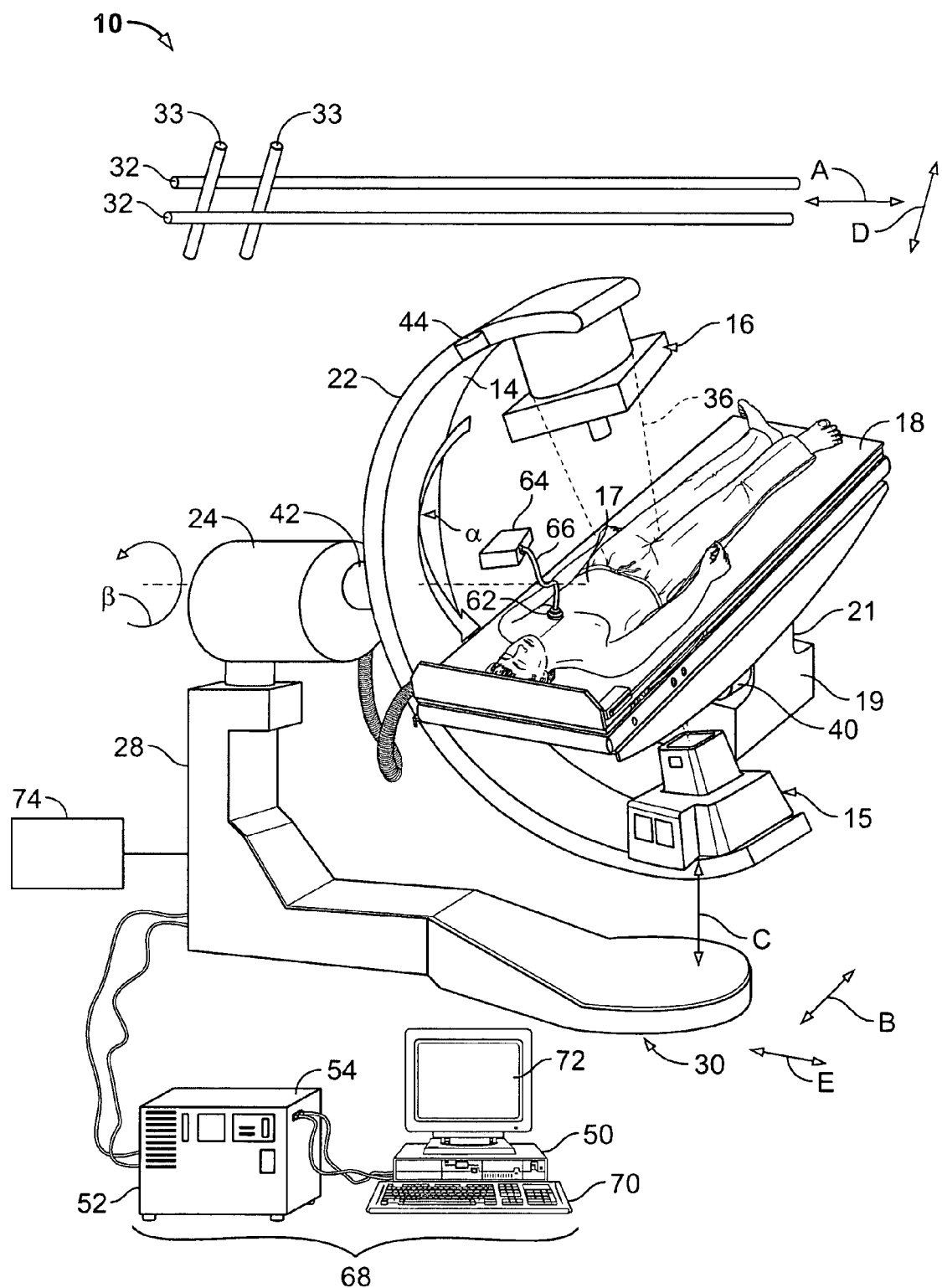
FIG. 1 is a schematic illustration of an imaging system in accordance with an embodiment of the present invention.

FIG. 1 is a schematic illustration of an imaging system 10 in accordance with an embodiment of the present invention. An X-ray source 15 and a dual X-ray/gamma ray detector 16 are attached to the two ends of a C-arm gantry 14. X-ray source 15 generates X-rays when applied with a high voltage (e.g., 10,000 to 140,000 volts) from a high voltage (HV) generator 74. For example, the X-ray source 15 may generate a cone-beam of X-ray photons that are projected from X-ray source 15 towards dual X-ray/gamma ray detector 16 in a diverging conical projection at a predetermined fan angle. Alternatively, the X-ray source 15 generates a fan beam of X-ray photons. Dual X-ray/gamma ray detector 16 may be fabricated of a flat panel Cadmium Zinc Telluride (CZT) semiconductor. A photoconduction process within the CZT semiconductor generates electron-hole pairs in an interaction with X-rays and/or gamma photons. The electron-hole pairs move to respective electrodes to be output as an electrical signal comprising photon count and energy data.

In imaging an object 17, such as a patient, the object 17 is placed on a patient table top 18 of a bed 19 and is positioned between the X-ray source 15 and the dual X-ray/gamma ray detector 16. The object 17 may include a radiopharmaceutical that concentrates in a predetermined region of the object 17 and emits emission gamma rays (not shown in FIG. 1). As the C-arm gantry 14 rotates, the object 17 may be imaged with X-rays over a predetermined arc such that a plurality of image views are received, while the object 17 remains positioned substantially directly between the X-ray source 15 and dual X-ray/gamma ray detector 16. A field of view of imaging system 10 may be established by a width of the dual X-ray/gamma ray detector 16 in a plane of rotation. Dual X-ray/gamma ray detector 16 may be translated in this plane to facilitate increasing an effective field of view of imaging system 10 during the rotation. Dual X-ray/gamma ray detector 16 may be included in a plurality of imaging assembly modalities and/or multi-modality imaging assemblies, for example, any combination of a SPECT imaging assembly, a PET imaging assembly, a CT imaging assembly, a Static X-ray imaging assembly, and a Dynamic (Fluoroscopy) X-ray imaging assembly. Bed 19 may have a table top slide/ascent and descent mechanism 21 for sliding the table top 18 in a forward and a backward direction B, in a sideways direction E, and in a vertically ascending and a descending direction C.

To be able to freely change the imaging direction of object 17, the gantry 14 is slidably rotatable in a direction α (alpha) along a circumference of the gantry 14 using a C-arm holder 22, and is rotatable in a direction β (beta) using a holder base 24. The axes of rotation of the directions α and β are substantially perpendicular to each other.

Holder base 24 may be coupled to a suitable support structure (not shown), such as a wall, a floor, and/or a ceiling, through a support base 28. Support base 28 may be supported to allow for slidable operation along arrows A and D using two systems of rails 32 and 33. The rails 32 and 33 are illustrated separate from the support base 28, and may be coupled to a bottom side 30 or the support base 28. The rails 32 and 33 may be coupled to the ceiling, the floor, or cantilevered from the wall, and may be perpendicular with respect to each other. Therefore, the position of the object 17 may be changed with respect to the C-arm gantry 14 by moving one or more components of the imaging system 10 in the directions of arrows A through D, and/or by moving the table top 18 in the direction of arrow E.

The imaging system 10 uses a volume CT scanning portion to examine the object 17 (e.g. a human patient, an animal patient, or an inanimate object) using a cone shaped beam 36 which traverses a set of paths across the object 17. The X-ray source 15 and dual X-ray/gamma ray detector 16 are mounted on the C-arm gantry 14 that rotates around the object 17 being examined. By way of example only, an operating voltage for the X-ray source 15 is obtained from the HV generator 74 in such a manner that the X-ray source 15 generates cone-shaped beam 36 of X-ray radiation when the HV is applied to it. Alternatively, an X-ray opaque shutter (not shown) is used to substantially block an emission of X-rays from the X-ray source 15, for example, when the X-ray source 15 is used in a continuous on mode while still modulating the emission of X-rays.

Cone-shaped beam 36 of radiation generated by the X-ray source 15 is projected through the object 17 being scanned. Dual X-ray/gamma ray detector 16 measures the X-ray radiation transmitted along paths across the cone-shaped beam 36.

The C-arm gantry 14 may be rotated in direction α and/or β to cause X-ray source 15 and dual X-ray/gamma ray detector 16 to rotate around the object 17 while images are being taken, both in a transmission X-ray portion of a scan and an emission gamma portion of a scan. Rotation, tilting, and relative linear motion between dual X-ray/gamma ray detector 16 and object 17 permits any desired data acquisition geometry, including, for example, a circle, a circle plus arc, and a circle plus line, a circle plus multiple lines, a circle plus multiple arcs, a spiral, and a 180 degree plus fan width geometry.

A sensor 40 coupled to the bed 19 detects a position of the patient table top 18 with respect to the bed 19 in each direction B, C, and E. A sensor 42, which may include a rotary encoder, detects rotational direction β and a sensor 44, which may include a linear encoder, detects the gantry 14 travel along axis α of C-arm holder 22. An output of each sensor may be transmitted to a processor 50 through a control interface 52. The processor 50 may generate control signals for controlling the position of the bed 19 and C-arm gantry 14 during a scan based on the sensor outputs, based upon for example, user inputs or a predetermined scan.

During a scan, volume data from a CT portion of a scan and from a SPECT portion of a scan is transmitted from dual X-ray/gamma ray detector 16 to processor 50 through a data interface 54. The processor 50 and associated hardware and software used to acquire and process data may be collectively referred to as a work station 68. The work station 68 has a keyboard 70 and/or other input devices such as a mouse, a pointer, and the like, and a monitor 72. The monitor 72 displays image data and may accept input from a user if a touchscreen is available.

For example, when operating in a cardiac gating mode, the CT portion of the scan and/or the SPECT portion of the scan may be gated from a signal relative to a functioning of a heart 62 within the object 17. A heart monitor 64 may be connected to the object 17 through a conduit 66 to generate an output signal, which may be used to modulate the X-ray source 15 to synchronize transmission and/or emission image acquisition with a cardiac cycle of the heart 62. In the exemplary embodiment, the heart monitor 64 controls the level of HV to the X-ray source 15 to change an X-ray output of the X-ray source 15 relative to the functioning of the heart 62. Alternatively, the heart monitor 64 controls a position of an X-ray opaque shutter to reduce the X-ray output of the X-ray source 15 relative to the functioning of the heart 62.

Figure 2:
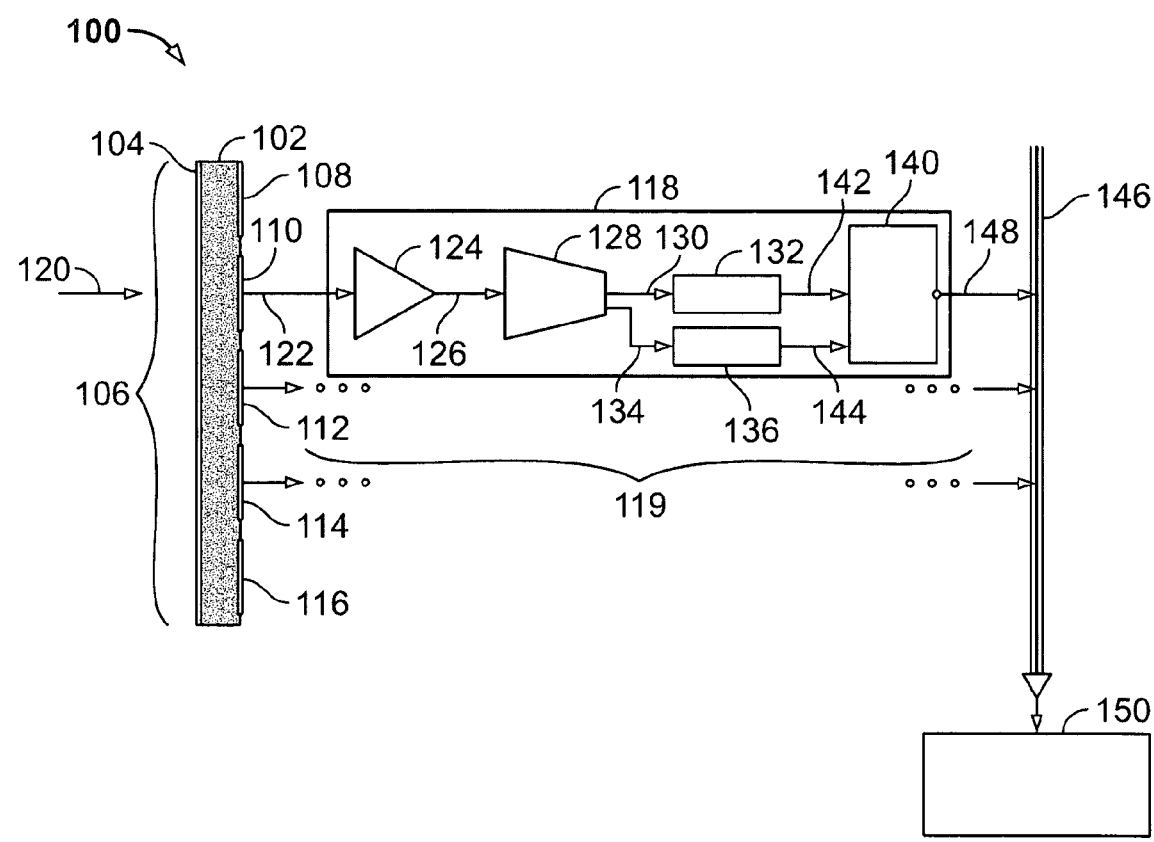
FIG. 2 illustrates a data channel within a block diagram of a detector in accordance with an embodiment of the present invention.

FIG. 2 illustrates a block diagram of a data channel 119 within a detector 100 in accordance with an embodiment of the present invention. The detector 100 may be the dual X-ray/gamma ray detector 16 discussed previously, thus having the capability of acquiring X-ray data, gamma ray data, or both simultaneously. The detector 100 may be formed of a matrix of crystals 102 formed of a solid state material such as CZT or a matrix of scintillation crystals each associated with a solid state photo-detector such as PIN or APD (Avalanche Photo Diode). Solid state materials such as CZT are sensitive to and capable of discriminating between transmission X-ray photons and emission gamma photons. A common cathode 104 is formed on one side of the crystals 102 and forms a detection field 106. Pixel anodes 108-116 are formed on a second side of the crystals 102. The pixel anodes 108-116 may form a matrix of rows and columns, wherein each pixel anode 108-116 is a location of a pixel. The matrix of crystals 102 may be equal or different sizes, such as 16×16 pixels or 8×18 pixels, wherein each pixel is, for example, 2 mm×2 mm or 2 mm×3 mm.

An electronic module 118 is attached in communication with each of the pixel anodes 108-116, forming a dedicated pixel data channel 119 associated with each pixel. The electronic module 118 may be an ASIC or other electronic device or devices. The single electronic module 118 interconnected with the pixel anode 110 is illustrated in FIG. 2, but it should be understood that an electronic module 118 may be connected to each of the pixel anodes 108-116. Optionally, the electronic module 118 may be interconnected with more than one pixel anode 108-116 and contain separate processing circuitry and/or capability for each pixel anode 108-116. Each electronic module 118 may receive signals from a subset of pixels from an area of the detector 100, such as an area having 16×16 pixels. Multiple ASICs may comprise multiple electronic modules 118 providing several (e.g. 128) channels, thus providing 128 pixel data channels 119 for receiving data from 128 pixels. The ASICs are connected to the bottom of the crystal 102, optionally using a carrier PCB. Alternatively, the electronic module 118 may be replaced by individual components performing equivalent functions.

Figure 3:
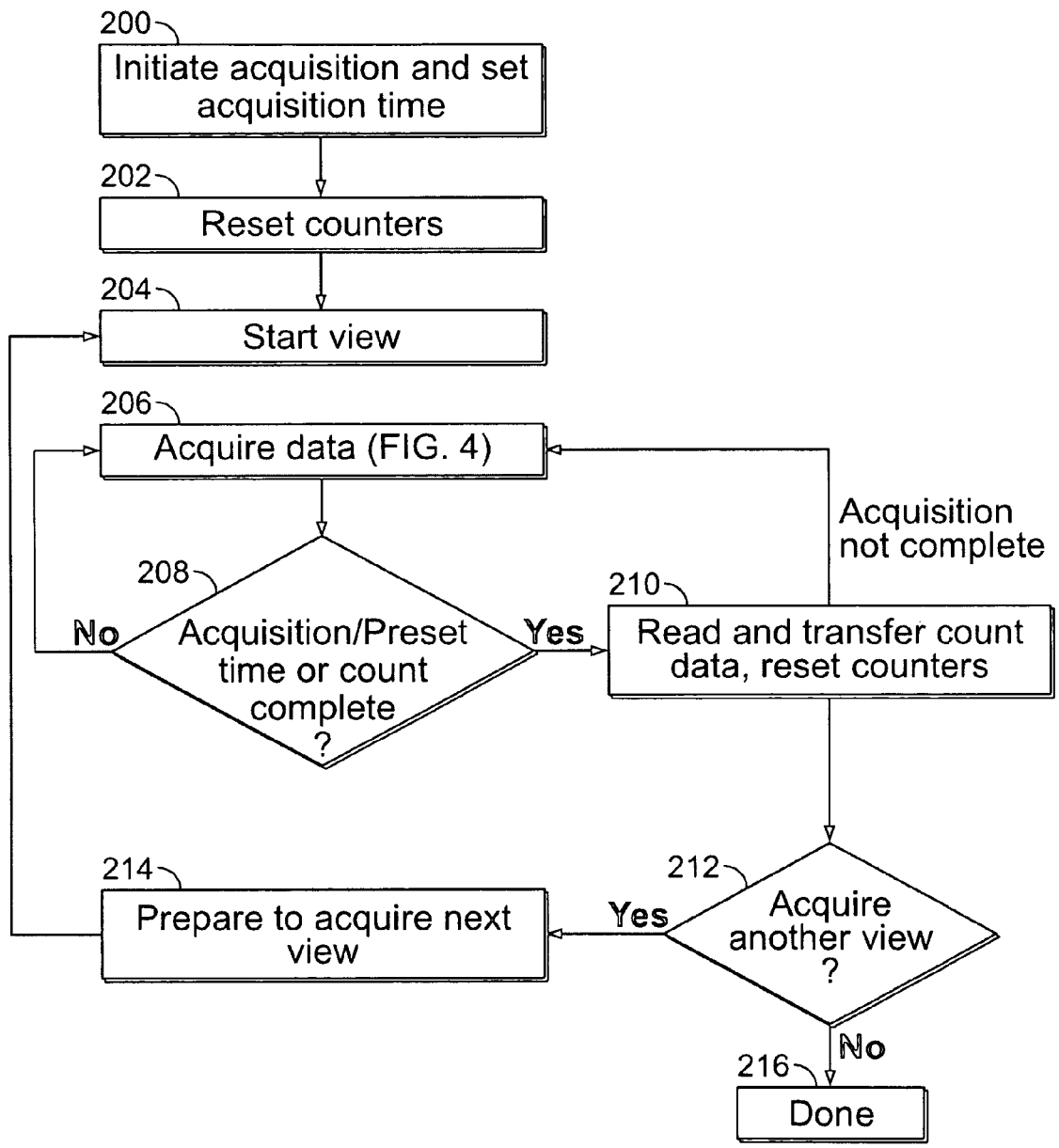
FIG. 3 illustrates a method for acquiring radiation events, such as X-rays or gamma rays, with the imaging system in accordance with an embodiment of the present invention.
Figure 4:
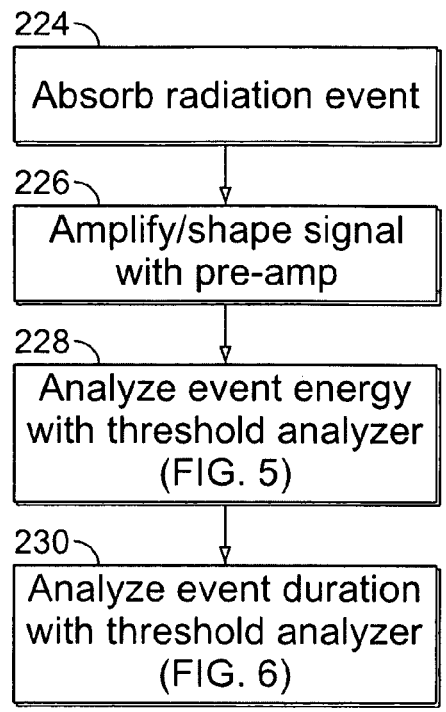
FIG. 4 illustrates a flow chart of the steps internal to the electronic module associated with each pixel in accordance with an embodiment of the present invention.

FIG. 3 illustrates a method for acquiring radiation events 120, such as X-rays or gamma rays, with the imaging system 10 in accordance with an embodiment of the present invention. FIG. 4 illustrates a flow chart of the steps internal to the electronic module 118 associated with each pixel in accordance with an embodiment of the present invention. The acquisition processes associated with the imaging system 10 (FIG. 3) and the electronic module 118 (FIG. 4) have been separated for clarity, but will be discussed together with FIG. 2.

In step 200, the imaging system 10 initiates an acquisition of radiation events 120 for an image view or frame of data. For example, an acquisition protocol, which may be specific to the anatomy being scanned and is stored on a memory device within the work station 68, may queue a series of image views to be acquired consecutively. Alternatively, a user may initiate the acquisition of one or more image views manually, such as through the keyboard 70 or a touchscreen (monitor 72).

In step 202, first and second (N) counters 132 and 136 within the electronic module 118 are reset to reflect that zero photons have been acquired. In step 204, the imaging system 10 starts a first view, and in step 206, data is acquired. In this exemplary embodiment, each of the counters, for example counters 132 and 136, counts X-ray events with energy within a specified range. Preferably, the specified ranges are contiguous and not overlapping.

Turning to FIG. 4, in step 224 a radiation event 120, such as an X-ray (FIG. 2) from the X-ray source 15 of FIG. 1, is absorbed at a pixel location, causing a signal at the pixel anode 110. The pixel anode 110 produces a signal 122 which is sent to a pre-amp 124 for amplification. The pre-amp 124 may be within the electronic module 118 as illustrated in FIG. 2 or may be a separate component. In step 226, the pre-amp 124 amplifies and shapes the signal 122. An amplified signal 126 comprising a pulse having at least an energy component and a pulse duration component indicative of the radiation event 120 is then passed to a threshold analyzer 128.

In step 228, the threshold analyzer 128 analyses the event energy of the amplified signal 126. Several types of analysis may occur depending upon acquisition type and the type of radiation (e.g. X-ray or gamma ray) currently being detected. X-ray energy, depending upon the setting of the HV generator 74 may range from 20 to 120 keV. By way of example only, with NM imaging, one or more isotopes may be used having a value within the range of 65 to 650 keV. NM gamma events occur at low rates. Each NM event is scrutinized carefully, preferably at the host computer, such as at the work station 68. To achieve this end, the signal is usually digitized and digital processing, such as energy correction, is performed on the result. Digitization of the signal may be done within the electronic module 118. Alternatively, an analog signal indicative of the event energy may be transmitted from the electronic module 118 to be digitized outside the electronic module 118. Therefore, if both gamma and X-ray are being acquired, there is a potential overlap in energies. However, as the level of HV and the energy of the isotopes being used are known, one or more thresholds can be determined by the detector 100 and imaging system 10. The NM rate or flux is about 1 Hz per pixel, while the X-ray flux during a CT scan may start at a low rate of about 1 MHz per pixel. As the X-ray flux is much greater than the NM flux, if an overlap of energy ranges occurs during a scan, the X-ray source 15 is turned off during the NM acquisition. However, the NM flux is negligible with respect to the X-ray flux, and thus does not interfere with the CT acquisition. If a separate NM scan is performed, Compton scattered gamma radiation events caused by the NM isotope but counted as X-ray may be counted and subtracted from the CT scan.

In NM mode, energy is analyzed in detail, but the analysis typically occurs at the work station 68. For example, an energy correction map is used, one or more energy windows are used, and one or more counters are associated with each pixel anode 108-116. In contrast, in CT mode, the flux rate is high and the counters, such as the first and second counters 132 and 136, are at the detector 100 (e.g. integrated as an ASIC).

Figure 5:
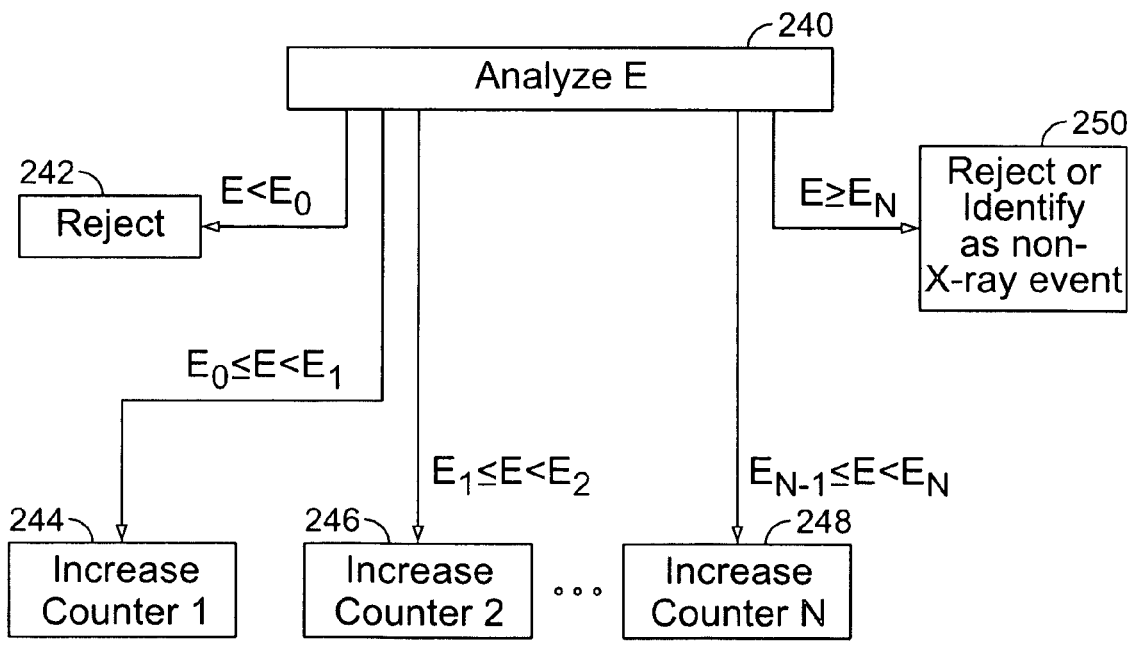
FIG. 5 illustrates a method for analyzing and counting valid photon events based on the photon's energy level in accordance with an embodiment of the present invention.

FIG. 5 illustrates a method for analyzing and counting valid photon events based on the photon's energy level in accordance with an embodiment of the present invention. In step 240, the threshold analyzer 128 of FIG. 2 analyzes the energy E of the radiation event 120 with respect to one or more threshold levels. If E is less than a minimum threshold $E_0$, the radiation event 120 may be rejected in step 242. Optionally, if E is greater than or equal to a maximum X-ray energy threshold $E_N$, such as 100 keV, the radiation event 120 may be identified as a "non-X-ray event" and may be processed as an NM event or may be rejected in step 250. $E_N$ may be based on the HV setting of the X-ray HV generator 74, or a fraction of the HV (e.g. 80% of the HV). Therefore, radiation events 120 which may be based on noise are not counted.

Alternatively, multiple counters may count each radiation event 120 that occurs within a specific energy range. Therefore, if E is greater than or equal to $E_0$ and less than a first energy threshold $E_1$, in step 244 the threshold analyzer 128 sends the signal 130 to the first counter 132 telling the first counter 132 to count the radiation event 120 as a valid event. If E is greater than or equal to $E_1$ and less than a second energy threshold $E_2$, in step 246 the threshold analyzer 128 sends a signal 134 to a second counter 136 telling the second counter 136 to count the radiation event 120 as a valid event. Although only the first and second counters 132 and 136 are illustrated in FIG. 2, the number of counters may be increased to count any number of energy ranges N, as demonstrated in FIG. 5. Thus, if E is greater than or equal to $E_{N-1}$ and less than an energy threshold $E_N$, in step 248 the threshold analyzer 128 tells the appropriate counter N to count the radiation event 120 as a valid event. In other words, the first counter 132, second counter 136, . . . N counter are dedicated counters which count each of the valid photons detected by the associated pixel. Each pixel has at least one dedicated counter 132. By counting each valid photon, better resolution may be achieved as no image data is lost or averaged. Energies $E_0, E_1, \ldots E_N$ may be specific for each pixel to reflect the variability in gain and bias of each pixel, individual pre-amp 124 and other components associated with the pixel. In this case, calibration may be performed.

In the case where one counter 132 is assigned to the entire X-ray energy range, if E is greater than the $E_1$ setting, the radiation event 120 may be assumed to be composed of two or more X-rays or may be a high-energy gamma event. How the radiation event 120 is treated may depend on the mode of operation, such as NM only, CT only or simultaneous NM and CT. If the radiation event 120 is being counted as an X-ray event, the threshold analyzer 128 sends a signal to a counter, such as signal 130 to the first counter 132, telling the first counter 132 to count the radiation event 120 as two (or more) valid events.

Figure 6:
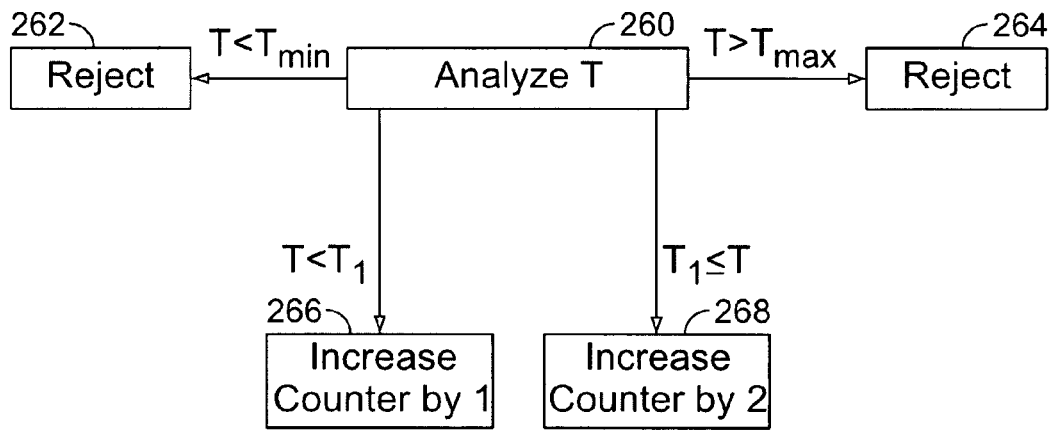
FIG. 6 illustrates a method for counting valid radiation events based on the pulse duration T in accordance with an embodiment of the present invention.

Returning to FIG. 4, in step 230, the threshold analyzer 128 analyzes a pulse duration T of the amplified signal 126. FIG. 6 illustrates a method for counting valid radiation events 120 based on the pulse duration T in accordance with an embodiment of the present invention. More than one pulse duration threshold may be used.

Optionally, the pulse duration T may be compared to one or both of a duration minimum and maximum. In step 260, the threshold analyzer 128 compares the pulse duration T to a duration minimum $T_{MIN}$. If T is less than $T_{MIN}$, the radiation event 120 is not a valid event and is rejected in step 262. Similarly, if T is greater than a maximum duration $T_{MAX}$, the radiation event 120 is not valid and is rejected in step 264.

A threshold $T_1$ may be set based on the duration of an average photon (e.g. approximately a microsecond). If T is less than $T_1$, in step 266 the threshold analyzer 128 sends the signal 130 to the first counter 132 telling the first counter 132 to count the radiation event 120 as one valid event. If T is greater than or equal to $T_1$, in step 268 the threshold analyzer 128 sends the signal 130 to the first counter 132 telling the first counter 132 to count the radiation event 120 as two valid events.

Flow returns to step 208 of FIG. 3, where the work station 68, a CPU, and the like determines whether the acquisition time, a predetermined time or total number of desired counts is complete. If one of the completion parameters is not met, flow returns to step 206. For example, a preset time or number of counts may be set to transfer count data more than once during the acquisition of a single view. If the acquisition or preset time has elapsed, or the desired count has been satisfied, flow passes to step 210.

In step 210, a multiplexer 140 reads the count data from the first and/or second (Nth) counters 132 and 136 via lines 142 and 144, respectively, and transfers the count data to a readout bus 146 via line 148. The counters 132 and 136 are reset to zero after being read. The readout bus 146 then transfers the data to the work station 68. Optionally, the work station 68 may periodically send a request for each pixel data channel 119 to send the count data from the counters 132 and 136, and then request that the counters 132 and 136 are reset (step 202). Alternatively, the first and second counters 132 and 136 may be configured such that whenever one of the counters 132 and 136 reaches a predetermined value, the counter 132 or 136 resets to zero and sends a message to the work station 68 that the predetermined value has been reached. Then when the view is over, the values of the counters 132 and 136 are read, therefore accessing the complete number of counts when the counters 132 and 136 have not reach the predetermined value. Returning to step 210, if the acquisition is not complete, flow returns to step 206. If the acquisition is complete, flow passes to step 212.

In step 212, the work station 68, the application or a user determines whether another view is to be acquired. If yes, flow passes to step 214. The gantry 14 and detector 100 are prepared to acquire the next view, which may entail loading a software protocol and/or moving the C-arm holder 22, gantry 14, detector 100, table top 18 and/or bed 19. Flow returns to step 204 and the next acquisition is started. If no more views are to be acquired, flow passes to step 216 from step 212 and the method is complete.

It should be understood that once an acquisition is started in step 204, radiation events 120 are continuously being detected and analyzed. In other words, radiation events 120 may be detected simultaneously as previously detected radiation events 120 are being evaluated by the threshold analyzer 128, discarded, or added to a count total within one of the first and second counters 132 and 136, and the count information is being transferred. It also should be understood that a plurality of modules 118 are working in parallel, while a plurality of multiplexers 140 are synchronized as to prevent data collision on the bus 146.

Figure 7:
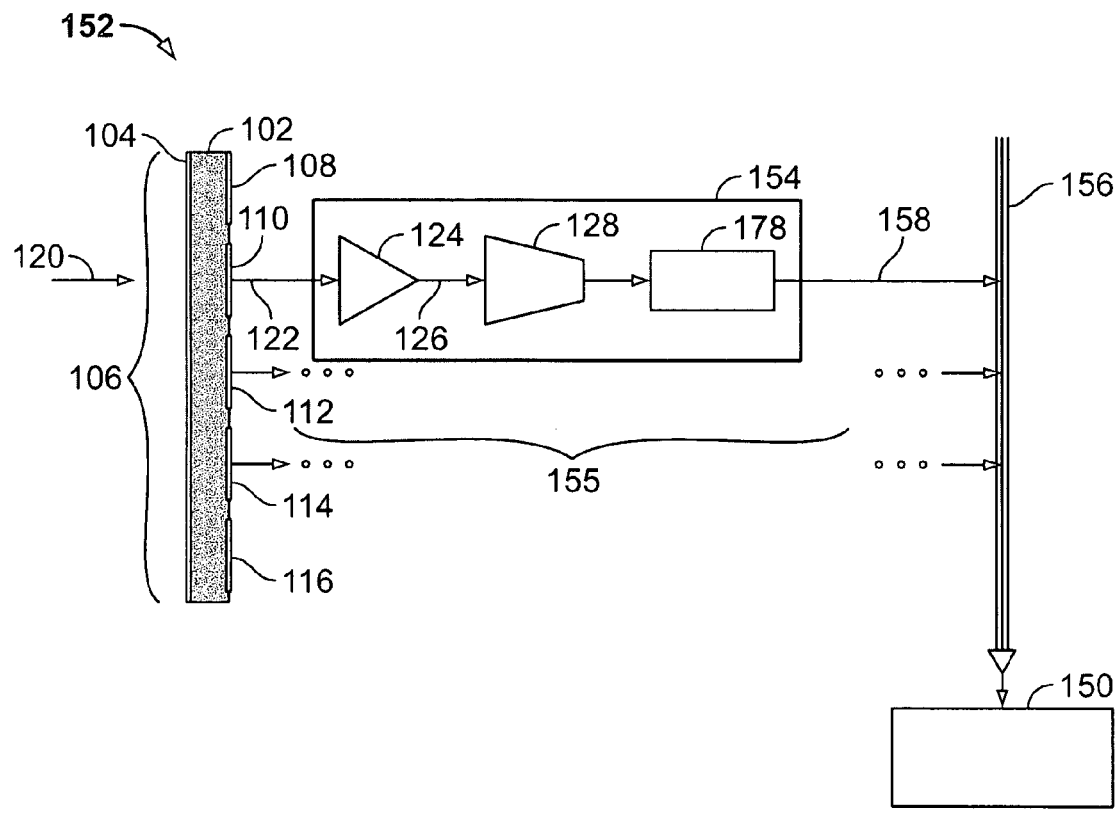
FIG. 7 illustrates a data channel within a detector comprising an ultra-fast readout bus formed in accordance with an embodiment of the present invention.

FIG. 7 illustrates a data channel 155 within a detector 152 comprising an ultra-fast readout bus 156 formed in accordance with an embodiment of the present invention. Components previously discussed in connection with FIG. 2 are indicated with the same item numbers.

In FIG. 7, an electronic module 154 comprises the pre-amp 124, the threshold analyzer 128 and an optional analog to digital converter (ADC) 178. The ADC 178 may be eliminated or bypassed if energy data from the radiation events 120 is not to be retained. Thus, the ADC 178 may be used to associate each event with energy information, such as when acquiring NM data. The electronic module 154 is interconnected with the pixel anode 110 in the same manner as previously discussed.

An ultra-fast readout bus 156 receives a signal via line 158 from the threshold analyzer 128 or the ADC 178 when a valid radiation event 120 has occurred. Because the ultra-fast readout bus 156 can process radiation events 120 as the radiation events 120 are acquired, it is not necessary to track the valid radiation events 120 with the first and/or second counters 132 and 136. By way of example only, more than one ultra-fast readout bus 156 may be interconnected with the detector 152, wherein each of the ultra-fast readout buses 156 read event data from a section of the detector 152, or a subset of the total number of pixel anodes 108-116.

Figure 8:
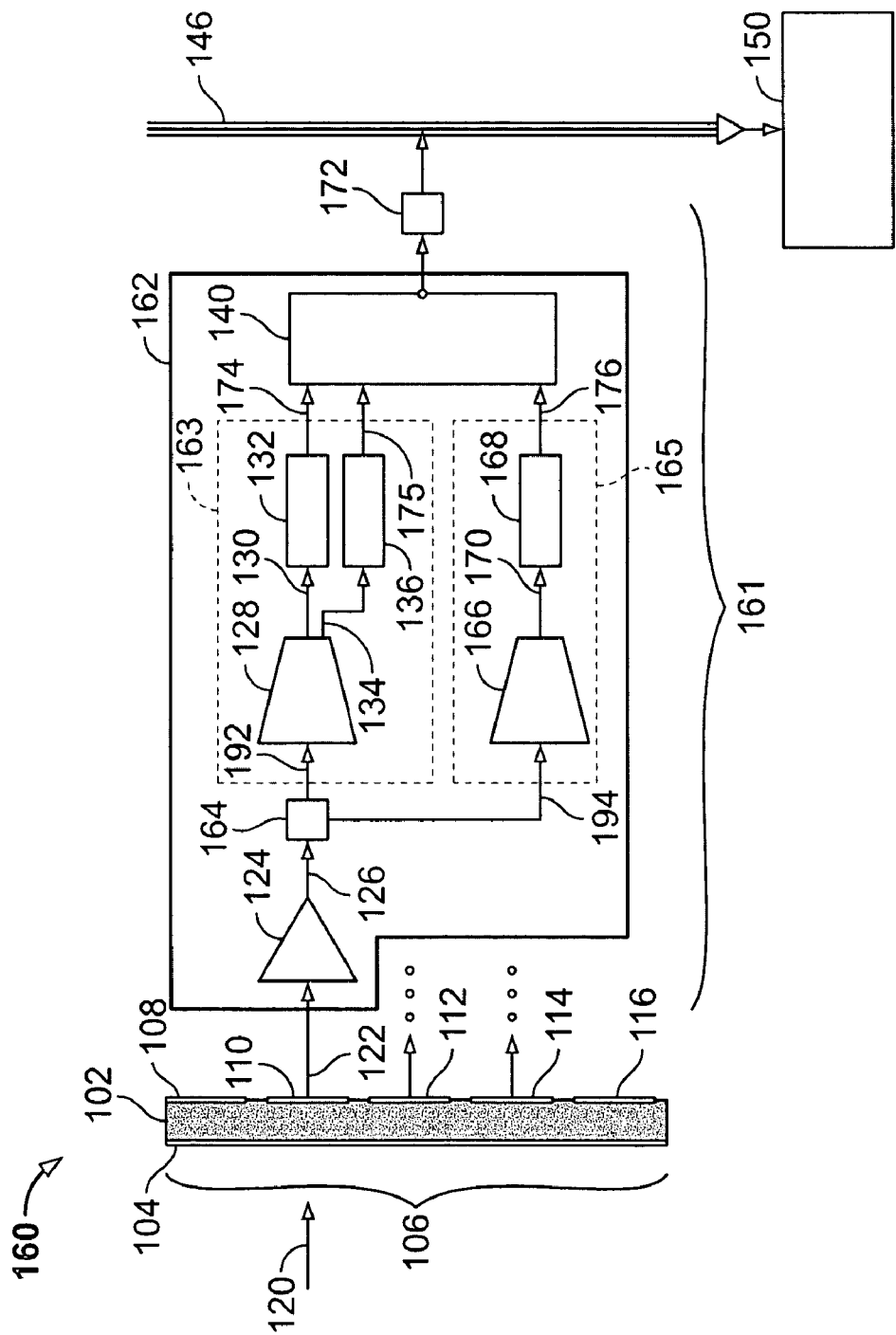
FIG. 8 illustrates a data channel within a detector comprising a mechanism for handling high count rates of radiation events which near or exceed a saturation rate, such as may be experienced during a CT scan, in accordance with an embodiment of the present invention.

FIG. 8 illustrates a data channel 161 within a detector 160 comprising a mechanism for handling high count rates of radiation events 120 which near or exceed a saturation rate, such as may be experienced during a CT scan, in accordance with an embodiment of the present invention. Elements in common with the detector 100 of FIG. 2 have been indicated with the same item numbers.

An electronic module 162 is interconnected with the pixel anode 110. The pre-amp 124 amplifies and shapes the signal 122, then passes the amplified signal 126 to a selector 164. The selector 164 is interconnected with a pulse counter sub-module 163 and a current detector sub-module 165. The selector 164 may be connected to both the sub-module 163 and 165 at all times, or one of the sub-modules 163 and 165 may be selected by a command from the imaging system 10. Alternatively, the selector 164 may select the pulse counter sub-module 163 when the flux is low and the current detector sub-module 165 when the flux is high. Flux may be estimated by the current flowing through the pixel or by time average of signal 126. For example, the selector 164 compares the rate at which the radiation events 120 are being received to a saturation rate. The saturation rate may indicate a lower saturation point at which either the pixel anode 110 or the components within the electronic module 162 become saturated, at which point not all radiation events 120 may be counted. By way of example only, pixels and/or their associated electronic modules 162 that acquire X-ray data along an edge of the object 17 or an area outside of the object 17 may quickly become saturated as the X-rays receive much less or no attenuation compared to X-rays traveling through a thicker portion of the object 17, such as a patient's torso. In some embodiments, the mode of operation of all or a plurality of groups of pixels is changed by a command. For example, if several electronic modules 162 are present within one ASIC, it may be preferable to change the operation of all selectors 164 within the same ASIC.

If the radiation events 120 are being received at a rate below the saturation rate, the amplified signal 126 is passed to the threshold analyzer 128 within the pulse counter sub-module 163 via line 192 for processing as discussed previously. If the radiation events 120 are being received at a rate nearing or exceeding the saturation rate, the selector 164 passes the amplified signal 126 to a current integrator 166 within the current detector sub-module 165 via line 194. The current integrator 166 measures a current level of the amplified signal 126, and thus the pixel is now operating in current mode. Therefore, it is not necessary to designate all or a portion of the detector 160 to operate in current mode and all valid events detected at individual pixels will be counted when below the saturation rate.

The current integrator 166 outputs an analog signal over line 170 to the analog to digital converter (ADC) 168. The ADC 168 outputs a signal indicative of the average current during the integration time of the current integrator 166. The output signal reflects the average rate of photons arriving at the pixel anode 110.

The first and second counters 132 and 136 and the ADC 168 output data to a multiplexer 140 over lines 174, 175 and 176. The multiplexer 140 may then output the data to the readout bus 146. Optionally, one or more buffers 172 may receive and hold data from the multiplexer 140 prior to outputting the data to the readout bus 146. For example, the buffer 172 may hold data until the readout bus 146 is available. It should be understood that the buffer 172 may also be used within the detectors 100 and 152 previously discussed in FIGS. 2 and 7. It is clear to a person skilled in the art that a plurality of separate buses may be used for data output over the lines 174, 175 or 176.

Figure 9:
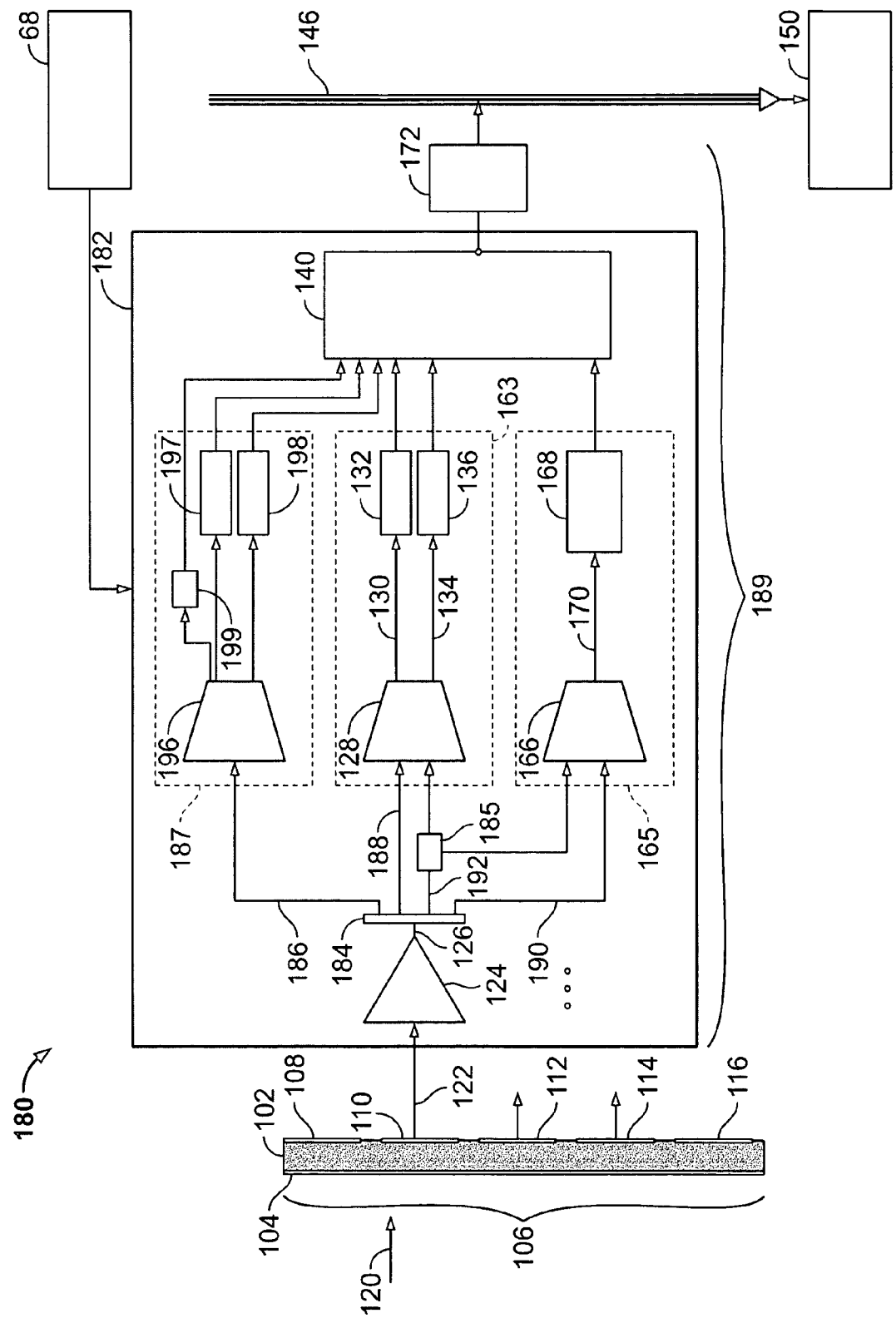
FIG. 9 illustrates a data channel for a pixel capable of detecting both NM and CT in accordance with an embodiment of the present invention.

FIG. 9 illustrates a data channel 189 for a pixel capable of detecting both NM and CT in accordance with an embodiment of the present invention. The data channel 189 is within a multi-modality detector 180 which is capable of being configured to acquire a multi-modality scan. The multi-modality detector 180 has elements in common with the previously discussed FIGS. 2, 7 and 8 which are indicated with like item numbers.

An electronic module 182 comprises different sets of circuitry for processing signals from different types of radiation. The electronic module 182 optionally has a first selector 184 which is interconnected with the pulse counter sub-module 163, the current detector sub-module 165 and an NM analyzer sub-module 187. The first selector 184 may be connected to each of the sub-modules 163, 165 and 187 at the same time, or the first selector 184 may receive a command from the work station 68 which selects one of the sub-modules 163, 165 or 187. Alternatively, some or all the sub-modules 163, 165 and 187 may be connected to the signal source (e.g. amplified signal 126) while some or none may be connected through the first selector 184.

The work station 68 may logically configure the multi-modality detector 180 so that subsets of the electronic modules 182 are configured to acquire different types of radiation data or to acquire radiation data in a different manner. For example, the first selector 184 may be a four-way switch wherein a first setting passes data along line 186 to the NM analyzer sub-module 187 for processing gamma rays. The NM analyzer sub-module 187 may comprise a threshold analyzer 196, first counter 197, and Nth counter 198 as previously discussed in FIG. 2. Alternatively, the threshold analyzer 196 may measure the energy of the signal and pass the data to an ADC 199. A second setting of the first selector 184 passes data along line 188 to the threshold analyzer 128 within the pulse counter sub-module 163 for processing X-rays in count mode, a third setting passes data along line 190 to the current integrator 166 within the current detector sub-module 165 for processing X-ray data in current mode, and a fourth setting passes data along line 192 to a second selector 185 where X-ray data is processed in count or current mode depending on the acquisition count rate as discussed previously in FIG. 8.

The first selector 184 receives the input signal and may further comprise circuitry to detect count rate. Therefore, if the count rate is determined to be a high rate, the first selector 184 may select to output data to one of lines 188, 190 or 192, while also processing data in accordance with the configuration of the multi-modality detector 180 (i.e. CT mode, NM mode, or simultaneous CT/NM mode).

For example, a small subset of the electronic modules 182 may be configured to acquire X-ray photons while a larger subset of the electronic modules 182 is configured to acquired NM (gamma) photons. In some cases, high energy NM photons and low energy X-Ray photons may be acquired simultaneously at the same pixel anode 108-116. The mode of operation is determined by a command from the work station 68 or by monitoring the type of signals arriving.

Figure 10:
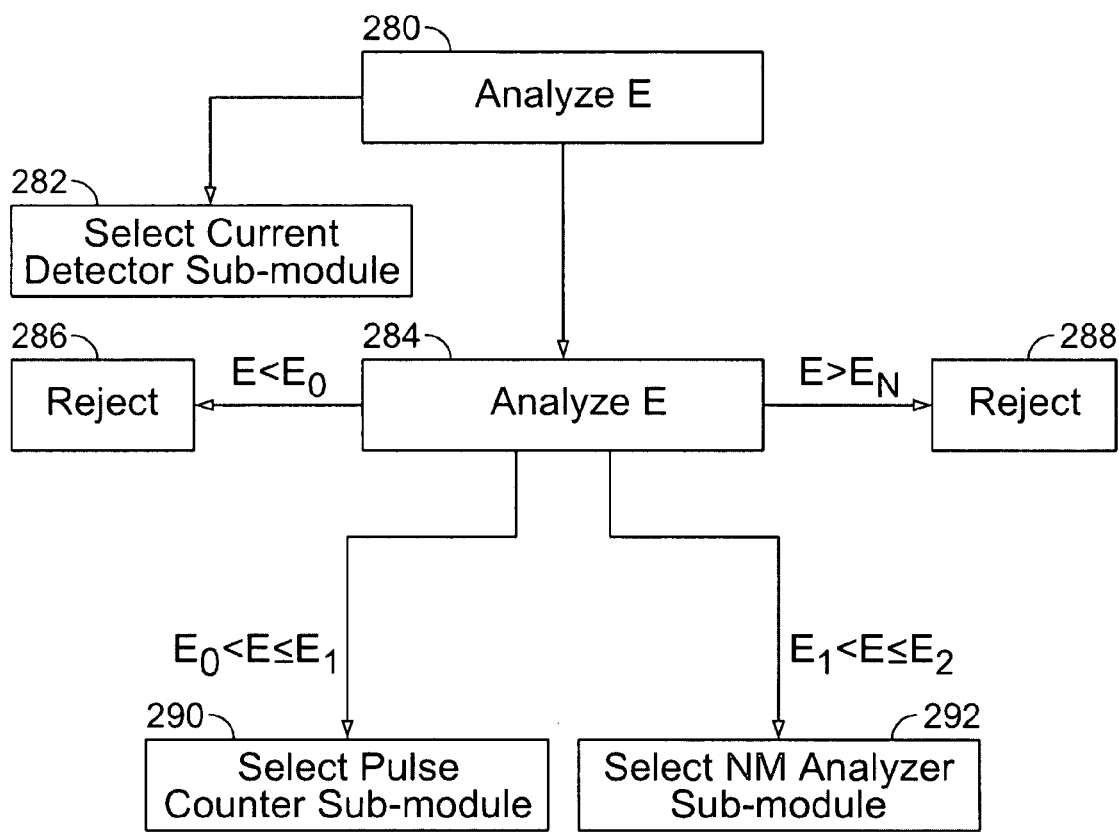
FIG. 10 illustrates a method for analyzing photon events using a data channel for a pixel capable of operating in both CT and NM, such as the data channel discussed in FIG. 9, in accordance with an embodiment of the present invention.

FIG. 10 illustrates a method for analyzing photon events using a data channel for a pixel capable of operating in both CT and NM, such as the data channel 189 discussed in FIG. 9, in accordance with an embodiment of the present invention. In step 280, the first selector 184 may compare the flux to a saturation threshold as discussed previously. If the flux is greater than the saturation threshold, flow passes to step 282 where the current detector sub-module 165 is selected. The input signal may be continuously monitored to determine whether it is greater or less than the saturation threshold.

If the input signal is less than the saturation threshold, flow passes to step 284. The threshold analyzer 167 analyzes the energy E of the radiation event 120 with respect to one or more threshold levels. The threshold levels may be determined by the energy of the isotope being used and/or may be based on the HV level. If E is less than a minimum threshold $E_0$, the radiation event 120 may be rejected in step 286. Optionally, if E is greater than a maximum energy threshold $E_N$, the radiation event 120 may be rejected in step 288.

If E is greater than or equal to $E_0$ and less than or equal to a first energy threshold $E_1$, in step 290 the radiation event 120 is passed to the pulse counter sub-module 163. If E is greater than the first energy threshold $E_1$ and less than or equal to a second energy threshold $E_2$, in step 292 the radiation event 120 is passed to the NM analyzer sub-module 187. The NM analyzer sub-module 187 may further analyze or process the signal, or transfer the signal to the work station 68 for further processing.

Figure 11:
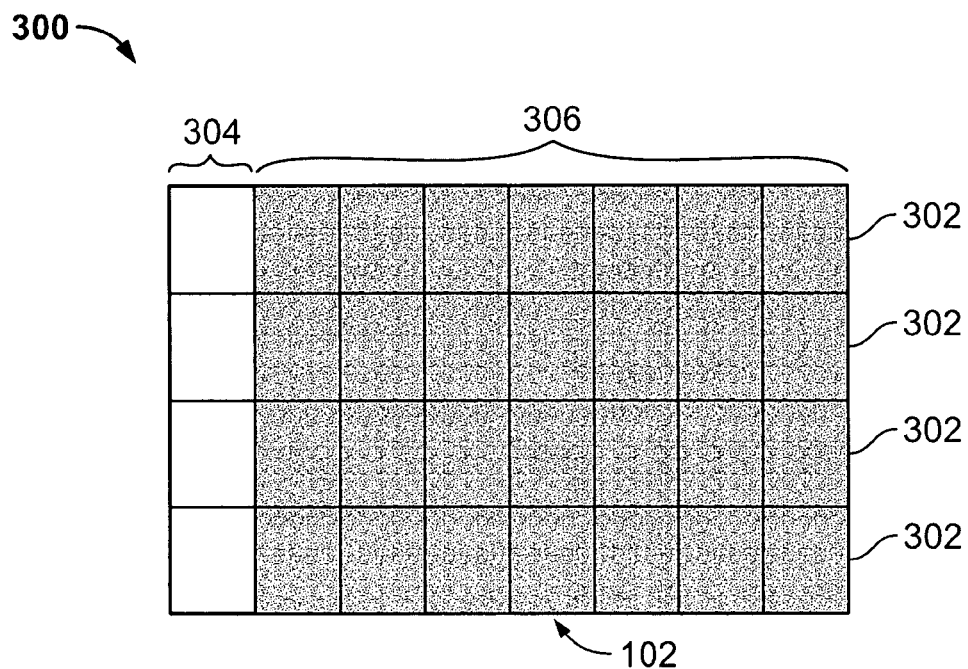
FIG. 11 illustrates a detector having a matrix of crystals arranged in rows and columns in accordance with an embodiment of the present invention.

FIG. 11 illustrates a detector 300 having a matrix of crystals 102 arranged in rows and columns in accordance with an embodiment of the present invention. Each crystal 102 is interconnected with an electronic module (not shown) such as the electronic module 182 of FIG. 9 to form a detector module 302. The term detector module 302 refers to the combination of an electronic module 182 and a crystal 102. Therefore, as previously discussed, multiple electronic modules 182 may be formed using a single ASIC. The detector modules 302 of detector 300 have been logically divided into a first subset 304 of the detector modules 302 and a second subset 306 of the detector modules 302. It should be understood that the electronic modules 182 or detector modules 302 formed within the same ASIC can be divided into different logical subsets.

By way of example only, the first subset 304 may acquire X-ray data in the count mode. The first subset 304 may also acquire X-ray data in the current mode if the rate of acquiring the radiation events 120 is near or exceeds the saturation rate. The second subset 306 may be used to acquire gamma photon data.

Figure 12:
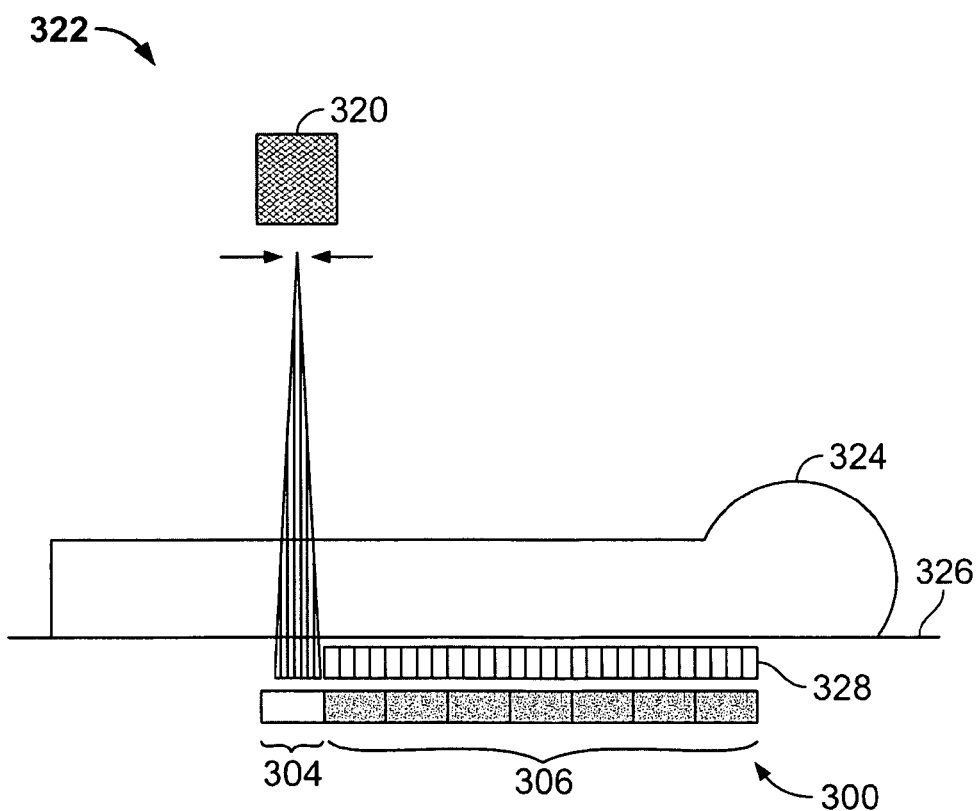
FIG. 12 illustrates a schematic side view diagram of the detector and an X-ray source used within a multi-modality system in accordance with an embodiment of the present invention.

FIG. 12 illustrates a schematic side view diagram of the detector 300 and an X-ray source 320 used within a multi-modality system 322 in accordance with an embodiment of the present invention. The multi-modality system 322 may include the C-arm gantry 14 as discussed in FIG. 1 or other appropriate gantry configuration. The detector modules 302 of the detector 300 are logically divided into the first subset 304 to acquire X-ray photon data and the second subset 306 to acquire gamma photon data as illustrated in FIG. 11. The second subset 306 is covered by a collimator 328 as is known in the art. A patient 324 may be placed on a table 326 between the detector 300 and the X-ray source 320. The patient 324 includes a radionuclide tracer, which is detected by the second subset 306.

Figure 13:
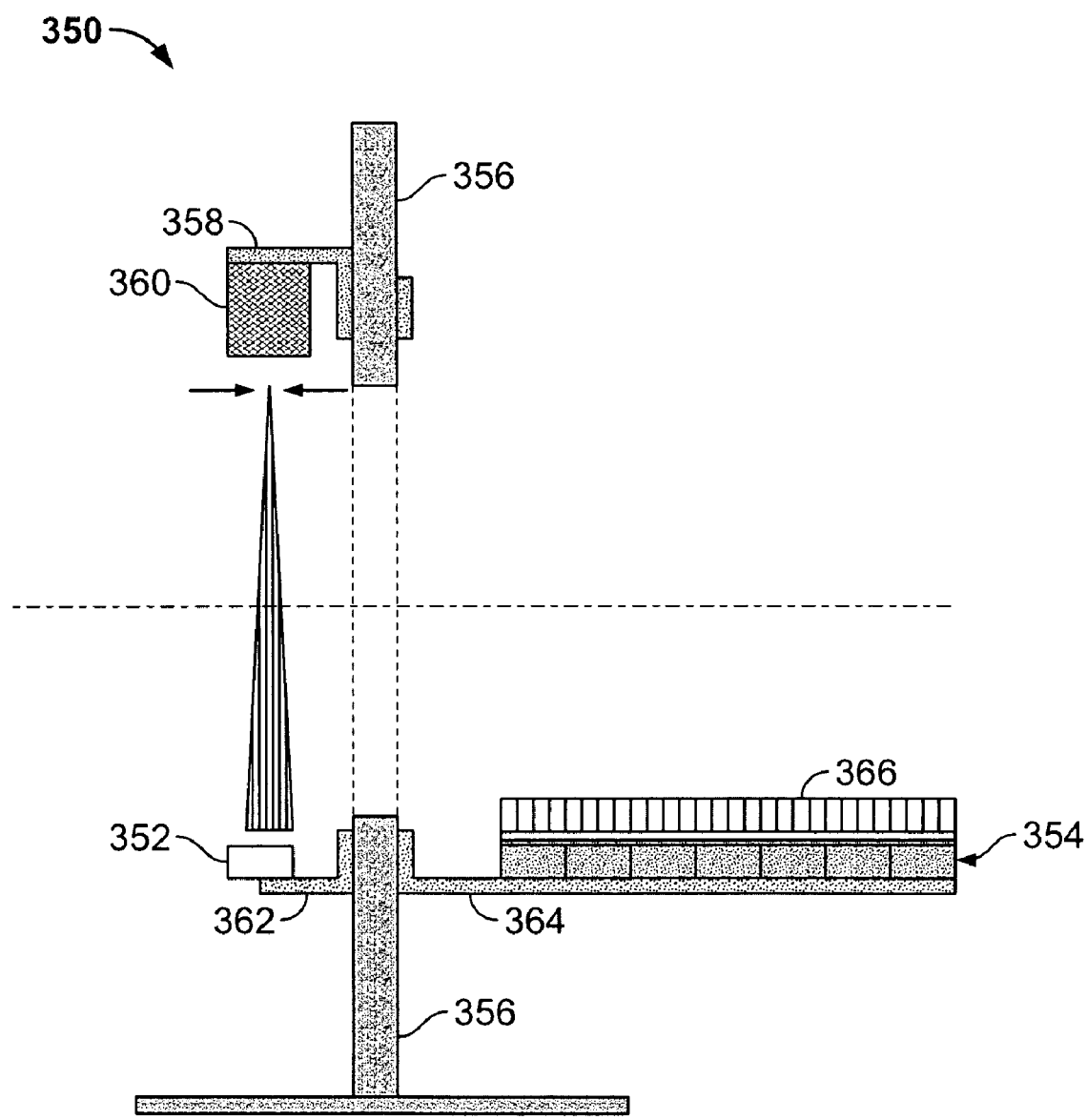
FIG. 13 illustrates a multi-modality system utilizing a first detector for acquiring X-ray photon data and a second detector for acquiring gamma photon data in accordance with an embodiment of the present invention.

FIG. 13 illustrates a multi-modality system 350 utilizing a first detector 352 for acquiring X-ray photon data and a second detector 354 for acquiring gamma photon data in accordance with an embodiment of the present invention. A common gantry stator 356 is interconnected with a first X-ray rotor 358 which supports and positions an X-ray tube 360. A second X-ray rotor 362 is interconnected with the common gantry stator 356 and supports the first detector 352. Also interconnected with the common gantry stator 356 is an NM rotor 364 which carries the second detector 354 and an associated collimator 366. By way of example, the first and second detectors 352 and 354 may be one of the detectors 100, 152, 160 or 180 as previously discussed. Alternatively, one of the detectors 352 and 354 may be a different type of detector used in the art to acquire the desired photon data. Each of the first and second detectors 352 and 354 comprise electronic modules, such as the electronic module 182 of FIG. 11, allowing each of the first and second detectors 352 and 354 to be reconfigured to acquired X-ray photon data, gamma photon data, or a combination of X-ray and gamma photon data.

Therefore, a multi-modality detector capable of acquiring more than one type of radiation data may be formed using electronics interconnected with each pixel of the detector. The detector may be logically configured to acquire two or more types of acquisitions simultaneously. Alternatively, the multi-modality detector may be combined in a system with one or more other detectors. The other detectors may also be multi-modality detectors, or may be detectors dedicated to acquiring radiation data for a single or dual modality, such as SPECT and/or PET. It should be understood that PET detection and imaging requires two opposing detector and timing circuitry to determine coincidence detection of a photon pair, in addition to NM detection capabilities. Timing may be achieved using an analog coincidence circuit, or by associating each NM detected event with a "time stamp" and digitally selecting pairs of events having time stamps within a predetermined time proximity of each other, as is known in the art.

A technical effect of the various embodiments of the invention is to acquire X-ray data, gamma ray data, or both simultaneously. The data events at each pixel of a detector may be analyzed and/or counted by a detector module interconnected with the pixel and within the detector. The data events may be compared to one or more thresholds for time and energy components. Additionally, each detector module may be configured to acquire a specific type of radiation data, or may process the data events based on count rate.

While the invention has been described in terms of various specific embodiments, those skilled in the art will recognize that the invention can be practiced with modification within the spirit and scope of the claims.

What is claimed is:

1. A detector for sensing and acquiring radiation data, comprising:
   solid state crystals forming a matrix of pixels and having a radiation detection field for sensing radiation events; and
   an electronic module being attached to each said pixel for counting said radiation events for each said pixel, said electronic module further comprising:
   a threshold analyzer for analyzing said radiation events, said threshold analyzer identifying valid events by comparing an energy level associated with said radiation event to a predetermined threshold; and
   at least first and second counters for counting said valid events, said threshold analyzer comparing said energy level to first and second energy ranges that comprise energy levels that are different with respect to each other, said first counter counting said valid events having an energy level within said first energy range and said second counter counting said valid events having an energy level within said second energy range and at least one of said first and second counters counting using increments greater than one when a duration of said valid event is greater than a duration threshold.

2. The detector of claim 1, wherein said radiation events being one of gamma photons and X-ray photons, said electronic module further comprising:
 a first set of circuitry for processing said gamma photons; and
 a second set of circuitry for processing said X-ray photons.

3. The detector of claim 1, wherein said radiation events being one of gamma photons and X-ray photons, said electronic module further comprising:
 a first set of circuitry for processing said gamma photons;
 a second set of circuitry for processing said X-ray photons; and
 a selector for selecting one of said first and second sets of circuitry based on a type of said radiation event.

4. The detector of claim 1, wherein said radiation events further comprising first and second types of radiation events, said threshold analyzer simultaneously identifying said valid events as one of said first and second types of radiation events.

5. The detector of claim 1, said electronic module further comprising:
 a selector for comparing a count rate of said radiation events to a saturation rate; and
 a current integrator for measuring a current associated with said radiation events if said count rate is greater than said saturation rate.

6. A system for sensing and acquiring radiation data, comprising:
 a detector comprising solid state crystals forming a matrix of pixels in rows and columns, said detector having a radiation sensing face for sensing radiation events, said detector further comprising electronic modules interconnected with said solid state crystals for counting said radiation events, said electronic modules comprising components for counting different types of radiation events, said electronic modules further comprising:
  a counter for counting said radiation events, each of said pixels being in communication with a dedicated said counter;
  a threshold analyzer for comparing a duration of said radiation event to a duration threshold, said counter increasing a count of said radiation events by a number greater than one when said duration of said radiation event is greater than said duration threshold;
 a gantry for holding said detector in a position with respect to an object; and
 a work station for receiving signal data representative of said radiation events.

7. The system of claim 6, further comprising an X-ray source for generating X-ray radiation events, said X-ray source being positioned opposite said detector and interconnected with said gantry.

8. The system of claim 6, further comprising:
 said detector further comprising first and second subsets of pixels; and
 said electronic modules further comprising first and second sets of components for acquiring first and second types of radiation events, said first set of components being in communication with said first subset of pixels and said second set of components being in communication with said second subset of pixels, said first set of components acquiring said radiation events representative of X-ray radiation emitted from an X-ray source and said second set of components acquiring radiation events representative of gamma radiation emitted from the object.

9. The system of claim 6, further comprising a second detector for acquiring radiation data, said radiation data being representative of at least one of PET, SPECT, CT, static X-ray imaging and dynamic X-ray imaging.

10. The system of claim 6, further comprising:
 said detector further comprising first and second detectors formed separate from one another; and
 said gantry further comprising first and second rotors, said first rotor supporting said first detector and said second rotor supporting said second detector.

11. A method for acquiring radiation events, comprising:
 detecting radiation events with a solid state detector comprising a matrix of pixels;
 comparing a duration of each of said radiation events to a threshold; and
 counting said radiation events at each said pixel with a dedicated counter, wherein said radiation events having said duration greater than said threshold are counted as two radiation events, each of said pixels being interconnected with said dedicated counter.

12. The method of claim 11, further comprising comparing an energy level of said radiation events to first and second energy ranges, said counting step further comprising counting said radiation events within said first energy range with a first counter and counting said radiation events within said second energy range with a second counter.

13. The method of claim 11, further comprising:
 storing a count of said radiation events in said dedicated counter;
 reading said count of said radiation events, said reading step being based on one of a predetermined time and a predetermined number of events; and
 resetting said dedicated counter.

14. The method of claim 11, further comprising:
 determining a rate of detection associated with said detecting step;
 comparing said rate of detection to a saturation rate threshold; and
 passing said radiation events to a current integrator when said rate of detection exceeds said saturation rate threshold.

15. The method of claim 11, further comprising:
 dividing said detector into first and second subsets of pixels;
 detecting said radiation events representative of gamma photons with said first subset of pixels; and
 detecting said radiation events representative of X-ray photons with said second subset of pixels.

16. The method of claim 11, further comprising:
 selecting a first counter to acquire said radiation events representative of a first type of radiation, said first counter being in communication with a first pixel anode; and
 selecting a second counter to acquire said radiation events representative of a second type of radiation, said second counter being in communication with said first pixel anode, said first and second types of radiation being different with respect to each other.

17. The method of claim 1, wherein the at least first and second counters compare a count of said valid events to a predetermined value, the at least first and second counters outputting a message when the count of said valid events exceeds the predetermined value.

18. The method of claim 1, wherein the at least first and second counter output a message indicating a count of said valid events after a predetermined time.

19. The method of claim 1, wherein the pixels are divided into first and second subsets of pixels, said first subset of pixels detecting said radiation events representative of a first type of radiation and said second subset of pixels detecting said radiation events representative of a second type of radiation.

20. The method of claim 6, the electronic module further comprising:
   a selector for comparing a count rate of said radiation events to a saturation rate; and
   a current integrator for measuring a current associated with said radiation events if said count rate is greater than said saturation rate.

* * * * *